United States Patent [19]

Chin et al.

[11] Patent Number: 5,595,958
[45] Date of Patent: Jan. 21, 1997

[54] 3-SUBSTITUTED PYRIDINE COMPOUNDS AND DERIVATIVES THEREOF

[75] Inventors: Hsiao-Ling M. Chin, Moraga; Nhan H. Nguyen, Richmond; David B. Kanne, Madera; David L. Lee, Pleasant Hill, all of Calif.

[73] Assignee: Zeneca Limited, London, England

[21] Appl. No.: 236,831

[22] Filed: May 2, 1994

[51] Int. Cl.⁶ .......................... A01N 43/40; C07D 401/06
[52] U.S. Cl. .......................... 504/250; 504/239; 504/242; 504/243; 504/252; 544/243; 544/298; 544/322; 544/333; 546/14; 546/22; 546/255; 546/261; 546/266
[58] Field of Search .................................. 504/239, 242, 504/243, 250, 252, 253; 544/180, 229, 298, 243, 322, 333; 546/255, 261, 262, 263, 275, 280, 281, 284, 14, 22, 266

[56] References Cited

U.S. PATENT DOCUMENTS

| | | | |
|---|---|---|---|
| 4,116,665 | 9/1978 | Krumkalns | 504/132 |
| 4,407,806 | 10/1983 | Cherpeck | 546/339 |
| 5,055,476 | 10/1991 | Effland et al. | 514/338 |
| 5,308,826 | 5/1994 | Chin et al. | 504/132 |

FOREIGN PATENT DOCUMENTS

| | | |
|---|---|---|
| 0101288 | 2/1984 | European Pat. Off. . |
| 0461079 | 12/1991 | European Pat. Off. . |
| 489670 | 6/1992 | European Pat. Off. . |

OTHER PUBLICATIONS

Radinov et al., "Synthesis of 4-Amino-3-pyridinyl and 4-Amino-5-pyrimidinyl Aryl Ketones and Related Compounds via an ortho Lithiation Reaction", *Synthesis*, pp. 886–891, Nov. 1986.
Marsais et al., "Directed Lithiation of 4-Halopyridines: Chemo-selectivity, Regioselectivity and Application to Synthesis", *J. Het. Chem.*, 25, pp. 81–87, Jan.–Feb. 1988.
Chemical Abstracts, vol. 93, No. 21, Nov. 24, 1980, Abstract No. 199233b, E. V. Krumkalns, "Composition for Inhibiting the Growth of Injurious Aquatic Weeds".
Wu, T., et al., "Synthesis and Herbicidal Activity of α-Heterocyclic Carbinol Carbamates," *J. Agric. Food Chem.*, 1987, vol. 35, No. 5, pp. 817–823.
Chemical Abstracts, vol. 108, No. 11, Abstract No. 94401e, Mar. 14, 1988, D. G. Cooper et al., "Preparation and formulation of 3-hydroxypyridines useful as histamine H1-antagonists," p. 646.
Chemical Abstracts, vol. 111, No. 15, Abstract No. 133951t, Oct. 9, 1989, P. Aube et al., "Trimethylsilanes. III. Characterization of an addition compound with aldehydes; preparation of animals and beta-dialkylamino-beta-aryl esters in aprotic media," p. 740.

Chemical Abstracts, vol. 110, No. 11, Abstract No. 95044u, Mar. 13, 1989, P. R. Huddleston et al., "Thiophene analogs of the alkaloids. Part 6. Synthesis of thiophene analogs of some 1-benzylisoquinolines," p. 690.
Chemical Abstracts, vol. 95, No. 15, Abstract No. 132848 7c, Oct. 12, 1981, R. G. Little, "Notes on the synthesis of meso-substituted porphyrins from pyrrol carbinols and the mechanism of the Rothemund reaction," p. 671.
Chemical Abstracts, vol. 112, No. 1, Abstract No. 7326a, Jan. 1, 1990, F. Sauter et al., "Fungicidal pyridine derivatives. I. alpha-(Trichloromethyl)-3-pyridinemethanols", p. 718.
Chemical Abstracts, vol. 60, No. 1, Jan. 6, 1964, V. G. Ermolaeva et al., "Pyridylthiazolylmethane series, III. Synthesis and properties of 3-pyridyl-2'-thiazolylcarbinols," col. 514b.
Chemical Abstracts, vol. 105, No. 3, Abstract No. 24110y, Jul. 21, 1986, L. B. Lam et al., "An acid–catalyzed hydroxyalkylation of uracil: A facile synthesis of 5-(arylhydroxymethyl)uracils," p. 625.
Chemical Abstracts, vol. 114, No. 25, Abstract No. 247091e, Jun. 24, 1991, M. Mallet, "Phenyllithium: novel metalating agents for pyridines," p. 742.
Chemical Abstracts, vol. 95, No. 21, Abstract No. 187017n, Nov. 23, 1981, T. Gungor et al., "Regioselective metalation in the pyridine series: original synthesis of 3-aroyl-2-aminopyridines", p. 632.

*Primary Examiner*—Yogendra N. Gupta
*Attorney, Agent, or Firm*—Marian T. Thomson; Joseph R. Snyder

[57] ABSTRACT

Herbicidal 3-substituted pyridine compounds and derivatives thereof of the formula:

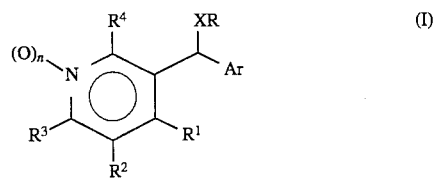

wherein Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon. Herbicidal compositions containing such 3-substituted pyridine compounds and derivatives thereof and methods of controlling undesirable vegetation employing these compounds and derivatives are also disclosed. The compounds in which XR is hydroxyl are also useful as intermediates for producing the disclosed 3-substituted pyridine derivatives.

16 Claims, No Drawings

3-SUBSTITUTED PYRIDINE COMPOUNDS AND DERIVATIVES THEREOF

FIELD OF THE INVENTION

In one aspect, this invention relates to novel 3-substituted pyridine compounds and derivatives thereof which exhibit unexpectedly desirable herbicidal activity. In other aspects, this invention relates to herbicidal compositions comprising a 3-substituted pyridine compound or derivative thereof and a suitable carrier, to a method of controlling undesirable vegetation comprising applying to the area where control is desired an herbicidally effective amount of a 3-substituted pyridine compound or derivative thereof and to intermediates useful in making such compounds.

BACKGROUND OF THE INVENTION

The need for effective herbicides needs no special emphasis. The control of weeds and undesirable vegetation is of great economic importance since weed competition inhibits the production of foliage, fruit or seed of agricultural crops. The presence of weeds can reduce harvesting efficiency and the quality of the harvested crop. Weeds on noncropped areas may cause a fire hazard, undesirable drifting of sand or snow, and/or irritation to persons with allergies. Thus, suppression of undesirable weed growth is very advantageous.

Accordingly, it is an object of this invention to provide effective novel herbicidal compounds, as well as to provide novel herbicidal compositions and novel methods of controlling weeds. Further, it is an object of this invention to provide intermediates which, as well as exhibiting herbicidal activity, are also useful in the production of other herbicidally active compounds.

While certain hydroxybenzyl-substituted nitrogen-containing heteroaryl compounds are disclosed in the art, these disclosures contain no description of the utility of such compounds. Thus, Radinov et al., "Synthesis of 4-Amino-3-pyridinyl and 4-Amino-5-pyrimidinyl Aryl Ketones and Related Compounds via an ortho-Lithiation Reaction", Synthesis, pp. 886–891 (November 1986), disclose inter alia at page 887, compounds of the formula

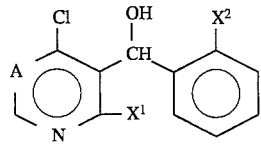

wherein A is CH or N, and when A is CH, $X^1$ is H and $X^2$ is hydrogen, chlorine or fluorine, and when A is N, $X^1$ is chlorine and $X^2$ is hydrogen.

Somewhat similarly, Marsais et al., "Directed Lithiation of 4-Halopyridines: Chemoselectivity, Regioselectivity and Application to Synthesis", J Heterocyclic Chem., Vol 25, pp. 81–87 (1987), disclose the production of compounds of the formula

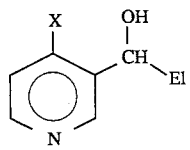

wherein El is phenyl or 2-methoxyphenyl.

Certain (non-substituted)-pyridyl-3-carbinols of the formula

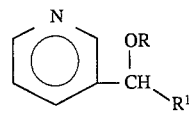

are disclosed in U.S. Pat. No. 4,407,806 to Cherpeck (wherein R and $R^1$ are as defined therein).

Similarly, U.S. Pat. No. 4,116,665 to Krumkalns discloses a method of regulating the growth of aquatic weeds employing compounds of the formula

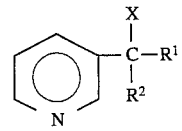

wherein, inter alia, $R^1$ may be hydrogen, $R^2$ may be (substituted)-phenyl and X may be hydroxyl or alkoxy.

Further, commonly owned U.S. Pat. No. 5,308,826, describes herbicidal 4-substituted pyridyl-3-carbinols.

SUMMARY OF THE INVENTION

In one aspect, this invention is directed to a compound of the formula (I):

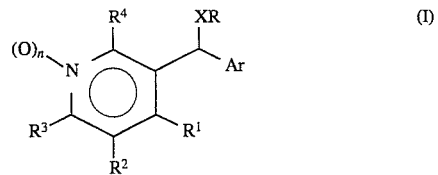

wherein:

Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon;

$R^1$, $R^2$, $R^3$ and $R^4$ are each independently hydrogen halogen, $C_1$–$C_6$ alkyl, $C_2$–$C_6$ alkenyl, $C_2$–$C_6$ alkynyl, nitro, cyano, hydroxy, thiocyano, —N($R^{11}$) ($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$–$C_6$ alkoxy or is of the formula —C(O)—$R^6$, —C(O)—C(O)—$R^6$, —S(O)$_2$—$R^6$, —P(O)($R^{11}$) ($R^{12}$) or —Si($R^{13}$) ($R^{14}$) ($R^{15}$);

wherein:

O is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$) ($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, (C$_1$–C$_6$)alkoxycarbonyl(C$_1$–C$_6$)alkyl, hydroxycarbonyl(C$_1$–C$_6$)alkyl, or N(R$^9$) (R$^{10}$) wherein R$^9$ and R$^{10}$ are each independently hydrogen, C$_1$–C$_6$ alkyl or phenyl;

or R$^7$ and R$^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with C$_1$–C$_6$ alkyl;

R$^{11}$ and R$^{12}$ are each independently C$_1$–C$_6$ alkyl, C$_1$–C$_6$ alkylthio or C$_1$–C$_6$ alkoxy;

R$^{13}$, R$^{14}$ and R$^{15}$ are each independently C$_1$–C$_6$ alkyl, C$_1$–C$_6$ alkoxy, C$_1$–C$_6$ haloalkyl, aryl or arylalkyl;

k is 0, 1 or 2;

n is 0 or 1;

and agriculturally acceptable salts thereof.

In another aspect, this invention is directed to a herbicidal composition comprising:

(A) a compound of the formula (I):

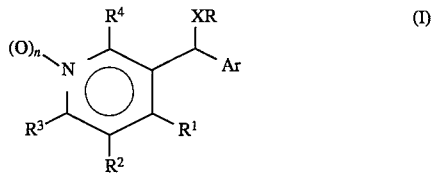

wherein:

Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon;

R$^1$, R$^2$, R$^3$ and R$^4$ are each independently hydrogen, halogen, C$_1$–C$_6$ alkyl, C$_2$–C$_6$ alkenyl, C$_2$–C$_6$ alkynyl, nitro, cyano, hydroxy, thiocyano, —N(R$^{11}$) (R$^{12}$), C$_1$–C$_6$ haloalkyl, C$_1$–C$_6$ alkoxy, C$_1$–C$_6$ haloalkoxy, (C$_1$–C$_6$)alkoxy-(C$_1$–C$_6$)alkyl, halo(C$_1$–C$_6$)alkoxy-(C$_1$–C$_6$)alkyl, —C(X)—R$^{10}$ or —S(O)$_k$—R$^{10}$;

X is oxygen or sulfur;

R is hydrogen, hydrocarbyl, hydrocarbyl substituted with one or more of halogen or C$_1$–C$_6$ alkoxy or is of the formula —C(O)—R$^6$, —C(O)—C(O)—R$^6$, —S(O)$_2$—R$^6$, —P(O) (R$^{11}$) (R$^{12}$) or -Si(R$^{13}$) (R$^{14}$) (R$^{15}$);

wherein:

O is oxygen or sulfur;

R$^6$ is hydrocarbyl, substituted hydrocarbyl, hydrocarbyloxy, substituted hydrocarbyloxy, hydrocarbyl-S—, substituted hydrocarbyl-S— or is of the formula —N(R$^7$) (R$^8$);

wherein R$^7$ and R$^8$ are each independently hydrogen, hydrocarbyl, substituted hydrocarbyl, hydrocarbyloxy, substituted hydrocarbyloxy, pyridyl, furyl, thienyl, (C$_1$–C$_6$)alkoxycarbonyl(C$_1$–C$_6$)alkyl, hydroxycarbonyl(C$_1$–C$_6$)alkyl, or N(R$^9$) (R$^{10}$) wherein R$^9$ and R$^{10}$ are each independently hydrogen, C$_1$–C$_6$ alkyl or phenyl;

or R$^7$ and R$^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with C$_1$–C$_6$ alkyl;

R$^{11}$ and R$^{12}$ are each independently C$_1$–C$_6$ alkyl, C$_1$–C$_6$ alkylthio or C$_1$–C$_6$ alkoxy;

R$^{13}$, R$^{14}$ and R$^{15}$ are each independently C$_1$–C$_6$ alkyl, C$_1$–C$_6$ alkoxy, C$_1$–C$_6$ haloalkyl, aryl or arylalkyl;

k is 0, 1 or 2; and n is 0 or 1 or an agriculturally acceptable salt thereof; and (B) a carrier therefor.

In yet another aspect, this invention is directed to a method for controlling undesirable vegetation comprising applying to the area where control is desired an herbicidally effective amount of a compound of the formula (I):

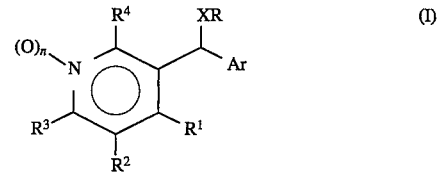

wherein:

Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon;

R$^1$, R$^2$, R$^3$ and R$^4$ are each independently hydrogen halogen, C$_1$–C$_6$ alkyl, C$_2$–C$_6$ alkenyl, C$_2$–C$_6$ alkynyl, nitro, cyano, hydroxy, thiocyano, —N(R$^{11}$) (R$^{12}$), C$_1$–C$_6$ haloalkyl, C$_1$–C$_6$ alkoxy, C$_1$–C$_6$ haloalkoxy, (C$_1$–C$_6$)alkoxy-(C$_1$–C$_6$)alkyl, halo(C$_1$–C$_6$)alkoxy-(C$_1$–C$_6$)alkyl, —C(X)—R$^{10}$ or —S(O)$_k$—R$^{10}$;

X is oxygen or sulfur;

R is hydrogen, hydrocarbyl, hydrocarbyl substituted with one or more of halogen or C$_1$–C$_6$ alkoxy or is of the formula —C(O)—R$^6$, —C(O)—C(O)—R$^6$, —S(O)$_2$—R$^6$, —P(O) (R$^{11}$) (R$^{12}$) or -Si(R$^{13}$) (R$^{14}$) (R$^{15}$);

wherein:

O is oxygen or sulfur;

R$^6$ is hydrocarbyl, substituted hydrocarbyl, hydrocarbyloxy, substituted hydrocarbyloxy, hydrocarbyl-S—, substituted hydrocarbyl-S— or is of the formula —N(R$^7$) (R$^8$);

wherein R$^7$ and R$^8$ are each independently hydrogen, hydrocarbyl, substituted hydrocarbyl, hydrocarbyloxy, substituted hydrocarbyloxy, pyridyl, furyl, thienyl, (C$_1$–C$_6$)alkoxycarbonyl(C$_1$–C$_6$)alkyl, hydroxycarbonyl(C$_1$–C$_6$)alkyl, or N(R$^9$) (R$^{10}$) wherein R$^9$ and R$^{10}$ are each independently hydrogen, C$_1$–C$_6$ alkyl or phenyl;

or R$^7$ and R$^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with C$_1$–C$_6$ alkyl;

R$^{11}$ and R$^{12}$ are each independently C$_1$–C$_6$ alkyl, C$_1$–C$_6$ alkylthio or C$_1$–C$_6$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl;

k is 0, 1 or 2; and n is 0 or 1;

or an agriculturally acceptable salt thereof.

In yet a further aspect, because the compounds of this invention wherein XR is OH are useful intermediates for producing the other compounds of this invention, as well as possessing herbicidal activity, this invention is directed to compounds of the formula (II):

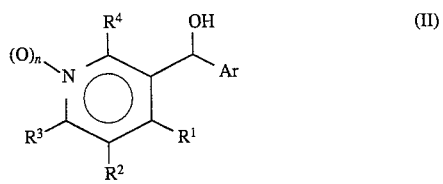

wherein:

Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon;

$R^1$, $R^2$, $R^3$ and $R^4$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

$R^{10}$ is hydrogen, $C_1$–$C_6$ alkyl or phenyl;

$R^{11}$ and $R^{12}$ are each independently $C_1$–$C_6$ alkyl, $C_1$–$C_6$ alkylthio or $C_1$–$C_6$ alkoxy;

k is 0, 1 or 2;

n is 0 or 1;

and agriculturally acceptable salts thereof.

DETAILED DESCRIPTION OF THE PREFERRED EMBODIMENTS

The novel herbicidal compounds of this invention are of the formula (I):

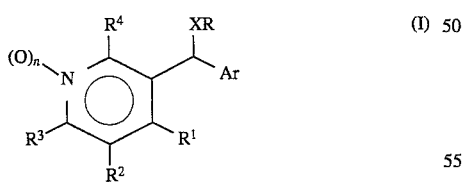

wherein:

Ar is a substituted or unsubstituted 5- or 6-membered heteroaryl group having 1, 2 or 3 ring nitrogen atoms with the remainder of the ring atoms being carbon; a substituted or unsubstituted 5-membered heteroaryl group having a ring heteroatom of oxygen or sulfur with the remainder of the ring atoms being carbon; or a substituted or unsubstituted 5-membered heteroaryl group having one ring nitrogen atom and either an oxygen or sulfur ring heteroatom with the remainder of the ring atoms being carbon.

$R^1$, $R^2$, $R^3$ and $R^4$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —N($R^{11}$)($R^{12}$), $C_1$–$C_6$ haloalkyl, ($C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy-($C_1$–$C_6$)alkyl, —C(X)—$R^{10}$ or —S(O)$_k$—$R^{10}$;

X is oxygen or sulfur;

R is hydrogen, hydrocarbyl, hydrocarbyl substituted with one or more of halogen or $C_1$–$C_6$ alkoxy or is of the formula —C(O)—$R^6$, —C(O)—C(O)—$R^6$, —S(O)$_2$—$R^6$, —P(O)($R^{11}$)($R^{12}$) or -Si($R^{13}$)($R^{14}$)($R^{15}$);

wherein:

O is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$)($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$)($R^{10}$) wherein $R^9$ and $R^{10}$ are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_1$–$C_6$ alkoxy;

$R^{13}$, $R^{14}$ and $R^{15}$ are each independently $C_1$–$C_6$ alkyl $C_1$–$C_6$ alkoxy, $C_1$–$C_6$ haloalkyl, aryl or arylalkyl;

k is 0, 1 or 2; and n is 0 or 1;

and agriculturally acceptable salts thereof.

Preferably,

Ar is a substituted or unsubstituted pyridyl, pyrimidinyl, pyrrolyl, furyl, thienyl, pyrazinyl, thiazolyl, oxazolyl or triazinyl group;

$R^1$, $R^2$, $R^3$ and $R^4$ are each independently hydrogen halogen, $C_1$–$C_6$ alkyl, $C_1$–$C_6$ haloalkyl, $C_1$–$C_6$ alkoxy, $C_1$–$C_6$ haloalkoxy, nitro or —S(O)$_k$—($C_1$–$C_3$)alkyl wherein k is 0, 1 or 2, with at least one of $R^1$, $R^2$, $R^3$ and $R^4$ not being hydrogen;

X is oxygen; and

R is of the formula

wherein $R^6$ is $C_1$–$C_{12}$alkyl, $C_1$–$C_6$ haloalkyl, phenyl or is N($R^7$)($R^8$), wherein $R^7$ and $R^8$ are each independently $C_1$–$C_{12}$ alkyl, hydrogen, $C_2$–$C_{12}$ alkenyl, $C_2$–$C_{12}$ alkynyl, $C_1$–$C_{12}$ haloalkyl, $C_1$–$C_6$ alkoxy, ($C_1$–$C_6$)alkoxy($C_1$–$C_6$)alkyl or $R^7$ and $R^8$ together with the nitrogen to which they are bound form a morpholine, piperidine or pyrrolidine ring.

More preferably,

Ar is a substituted or unsubstituted pyridyl, pyrimidinyl, pyrrolyl, furyl, thienyl, pyrazinyl, thiazolyl, oxazolyl or triazinyl group;

$R^1$ is trifluoromethyl, fluoro, chloro, bromo, iodo, methoxy, methyl or ethyl;

R², R³ and R⁴ are each independently hydrogen, chloro or bromo;

X is oxygen; and

R is of the formula

wherein R⁶ is $C_1-C_6$ alkyl or is of the formula $N(R^7)(R^8)$, wherein R⁷ and R⁸ are independently hydrogen, $C_1-C_6$ haloalkyl, $C_1-C_6$ alkyl or $C_2-C_6$ alkenyl.

The term "substituted . . . heteroaryl group" as used in the definition of Ar is intended to include heteroaryl groups, as defined above, having one or more substituents independently selected from the group consisting of halogen, $C_1-C_6$ alkyl, $C_2-C_6$ alkenyl, $C_2-C_6$ alkynyl, $C_1-C_6$ alkoxy, $C_1-C_6$ alkylcarbamylthio, mercapto, $C_1-C_6$ haloalkyl, $C_1-C_6$ haloalkoxy nitro, cyano, hydroxy, thiocyano, $(C_1-C_6)$alkoxy-$(C_1-C_6)$ alkyl, $-S(O)_k-R^{10}$ or $-N(R^{11})(R^{12})$, wherein k, $R^{10}$, $R^{11}$ and $R^{12}$ have the meanings set forth above; and to include N-oxides of the heteroaryl group. Of these substituents, halogen, $C_1-C_6$ alkyl, $C_1-C_6$ alkoxy and $C_1-C_6$ haloalkyl are especially preferred.

One group of preferred 3-substituted pyridine compounds is of the formula:

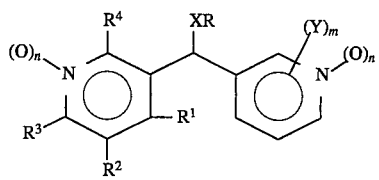

wherein

X, R, $R^1$, $R^2$, $R^3$, $R^4$ and n have the same meanings as in formula (I);

m is 0, 1, 2, 3 or 4; and when m is not 0, each Y is independently halogen, $C_1-C_6$ alkyl, $C_1-C_6$ haloalkyl, $C_1-C_6$ alkoxy, $C_2-C_6$ alkenyl, $C_2-C_6$ alkynyl, $C_1-C_6$ alkylcarbamylthio, mercapo, $C_1-C_6$ haloalkoxy, nitro, cyano, hydroxy, thiocyano, $(C_1-C_6)$-alkoxy-$(C_1-C_6)$alkyl, $-S(O)_k-R^{10}$ or $-N(R^{11})(R^{12})$, wherein k, $R^{10}$, $R^{11}$ and $R^{12}$ have the meanings set forth above.

Another group of preferred compounds is 3-substituted pyridines of the formula:

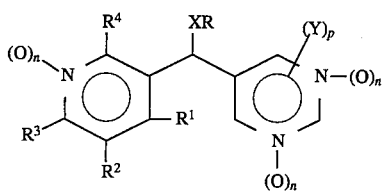

wherein X, R, $R^1$, $R^2$, $R^3$, $R^4$ and n have the same meanings as set forth above;

is 0, 1, 2 or 3; and when p is not 0, each Y has the same meaning as set forth with respect to formula (III).

Yet another group of preferred compounds is 3-substituted pyridines of the formula:

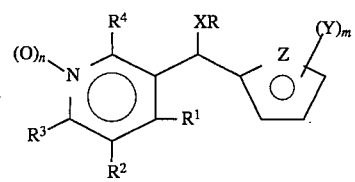

wherein

Z is nitrogen, oxygen or sulfur; and

X, R, $R^1$, $R^2$, $R^3$, $R^4$, n, Y and m have the same meanings as set forth above with respect to formula (III).

A still further group of preferred compounds is 3-substituted pyridines of the formula

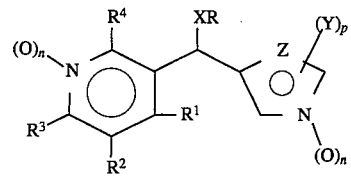

wherein Z is nitrogen, oxygen or sulfur; and X, R, $R^1$, $R^2$, $R^3$, $R^4$, n, Y and p have the same meanings as set forth above with respect to formula IV.

The formulae given above are intended to include tautomeric forms of the structures drawn therein, as well as physically distinguishable modifications of the compounds which may arise, for example, from different ways in which the molecules are arranged in a crystal lattice, or from the inability of parts of the molecule to rotate freely in relation to other parts, or from geometrical isomerism, or from intramolecular or intermolecular hydrogen bonding, or otherwise.

The compounds of such formulae can exist in enantiomeric forms. The invention includes both individual enantiomers and mixtures of the two in all proportions.

As is employed herein the term "hydrocarbyl", whether representing a substituent on its own or whether it is part of the definition of a larger group (e.g., as in hydrocarbyloxy, hydrocarbyl—$S(O)_k$—, etc.) is intended to include hydrocarbyl groups having from 1 to 12 carbon atoms. The term hydrocarbyl therefore includes, for example, $C_1$ to $C_{12}$ alkyl including both straight and branched chain isomers (e.g., methyl, ethyl, propyl, and hexyl); cycloalkyl of 3 to 12 carbon atoms (e.g., cyclopropyl, cyclobutyl and cyclohexyl); $C_2$ to $C_{12}$ alkenyl including for example allyl and crotyl; $C_2$ to $C_{12}$ alkynyl (e.g., propynyl); phenyl; phenylalkyl; alkylphenyl, alkenylphenyl, alkynylphenyl, alkylbenzyl, alkenylbenzyl, alkynyl benzyl, naphthyl and the like.

The term "substituted hydrocarbyl" is intended to include hydrocarbyl groups, as defined above, having one or more substituents selected from the group consisting of halogen (i.e., fluorine, chlorine, bromine, and iodine); $C_{1-4}$ alkoxy; $C_{1-4}$ alkyl-$S(O)_k$—; nitro; cyano; carboxy, and salts, amides and esters thereof; alkanoyl of 2 to 4 carbon atoms; and phenyl optionally substituted by one or more $C_{1-4}$ alkyl, $C_{1-4}$ alkoxy, $C_{1-4}$ alkyl-$S(O)_k$—, nitro, fluorine, chlorine, bromine, cyano, or $CF_3$ groups. In the above definitions, k is 0, 1 or 2.

Further, when the hydrocarbyl radical is a substituted aryl radical (e.g., phenyl, benzyl or naphthyl), the substituents may include one or more of the substituents listed in the last foregoing paragraph.

The expression "salts, amides, and esters thereof" used above in relation to carboxy substitution includes, for example, salts formed from alkali metal (e.g., sodium, potassium, and lithium), alkaline earth metals (e.g., calcium and magnesium), the ammonium ion, and substituted ammonium ions wherein one, two, three, or four of the hydrogen atoms have been replaced by optionally substituted $C_1$–$C_6$ hydrocarbyl moieties as defined above.

Further, in the above definitions the term "halogen" includes fluoro, chloro, bromo and iodo groups. In polyhalogenated groups the halogens may be the same or different.

Particularly preferred compounds include:
1,1-bis-(4-trifluoromethylpyrid-3-yl)-1-trimethylacetoxymethane;
1,1-bis-(4-trifluoromethylpyrid-3-yl)-1-N,N-dimethylcarbamyloxymethane;
1,1-bis-(4-trifluoromethylpyrid-3-yl)-1-N-ethylcarbamyloxymethane;
1,1-bis-(4-trifluoromethylpyrid-3-yl)-1-N-methylcarbamyloxymethane;
1-(4-trifluoromethylpyrid-3-yl)-1-(4-methoxypyrimidin-5-yl)-1-N,N-dimethylcarbamyloxymethane; and
1-(4-trifluoromethylpyrid-3-yl)-1-(4-methoxypyrimidin-5-yl)-1-N-ethylcarbamyloxymethane.

The compounds of the present invention have been found to be active herbicides, possessing utility as pre-emergence and post-emergence herbicides and useful against a wide range of plant species including broadleaf, grassy and perennial species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions.

The term "agriculturally acceptable salt" is easily determined by one of ordinary skill in the art and includes hydrohalogen, acetic, sulfonic, phosphonic, inorganic and organic acid salts.

In general, the compounds of this invention are prepared by (A) reacting a substituted pyridine compound with a substituted or unsubstituted heteroaryl carboxaldehyde in the presence of a suitable base to form a 3-substituted pyridine compound of formula (II) above; and, where appropriate, (B) reacting such 3-substituted pyridine compound with an appropriate derivatizing agent (e.g., an alkyl or aryl acid halide, carbamoyl halide, alkyl halide, sulfonyl halide or phosphoryl halide or trialkylsilylhalide) or an appropriate isocyanate, or sequentially first with phosgene or a phosgene equivalent and then with an appropriate amine, to produce the desired compound.

Typically, about 1–2 equivalents of an appropriate base (such as lithium diisopropyl amide or n-butyl lithium) and a substituted pyridine compound, as defined above, in a solvent (such as ethylene glycol dimethyl ether, tetrahydrofuran, diethyl ether or the like) are combined at a temperature of between about −100° and about 0° C. After suitable blending, about 1–2 equivalents of the heteroaryl carboxaldehyde are generally added.

This reaction mixture is typically agitated and slowly warmed up to ambient temperature (about 25° C.) over a period of 1–24 hours. The reaction may be quenched with an aqueous solution and the 3-substituted pyridine compound so produced may be recovered by conventional techniques (such as extraction, filtration and the like) and purified by known methods, e.g., flash chromatography.

In the second step, the 3-substituted pyridine compound of formula (II), in a suitable solvent (such as tetrahydrofuran, methylene chloride, or the like) may typically be added to between about 1 and about 4 equivalents of an appropriate base (such as sodium hydride or triethylamine) at about 0° C. Between about 1 and about 3 equivalents of derivatizing agent (such as a carbamoyl halide, an alkyl halide, a sulfonyl halide or a phosphosphoryl halide, an alkyl or aryl acid halide or trialkylsilyl halide) is then added and the mixture agitated until the reaction is complete. The reaction may be quenched by the addition of an aqueous solution, and the products recovered by conventional techniques, such as extraction, filtration and the like. The product so recovered may then be purified by conventional techniques such as flash chromotography or the like.

Alternatively, in the second step, the 3-substituted pyridine compound in suitable solvent (such as tetrahydrofuran, methylene chloride or the like) may be added to between about 2 and about 3 equivalents of an appropriate isocyanate. Between about 1 and about 10 mole percent of one or more appropriate catalysts, e.g., triethyl amine or dibutyl tin dilaurate, may be added and the reaction mixture agitated at between about 0° and 100° C. for an appropriate period (e.g., 2 to 24 hours). The product may be recovered by conventional techniques (such as extraction, filtration or the like) and may be purified by conventional techniques such as flash chromatography or the like.

The substituted pyridine starting materials are either commercially available or may be prepared by one of ordinary skill in the art employing methods such as those described in "Heterocyclic Compounds, Pyridine and Its Derivatives", R. A. Abramovitch, Vol. 14, Wiley, 1973. The substituted heterocyclic starting materials are commercially available or may be prepared employing techniques such as those described in T. Kelley, W. Xu and J. Sundareson, *Tetrahedron Letters*, 34, 6173 (1993) or as described below.

The herbicidal compositions of this invention comprise a compound of formula (I) above and a suitable carrier, which carriers are well known to one of ordinary skill in the art.

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other nonvolatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 4-benzoylpyrazole derivatives such as pyrazoxyfen, pyrazolate and benzofenap;

D. dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, flurogly-cofen or salts or esters thereof, nitrofen, bifenox, aci-fluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. triketone and cyclohexanedione herbicides such as alloxydim, sulcotrione and salts thereof, sethoxydim, cycloxydim, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl and diflufenican;

X. amino acid herbicides such as glyphosate and glufosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

\* These compounds are preferably employed in combination with a safener such as 2,2-dichloro-N,N-di-2-propenylacetamide (dichlormid).

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| | |
|---|---|
| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| | |
|---|---|
| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| Wettable powders: | |
|---|---|
| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
|---|---|
| 25%: | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

The amount of the present compositions which constitute a herbicidally effective amount depends upon the nature of the seeds or plants to be controlled. The rate of application of active ingredients varies from about 0.01 to about 25 pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to limit the scope of this invention in any manner whatsoever.

Example 1

Preparation of
1-(4-bromopyrid-3-yl)-1-(4-chloropyrid-3-yl)methanol
(Compound No. 5)

Five grams (g) of 4-chloropyridine hydrochloride were placed into a 30 milliliters (ml) of diethyl ether in a 200 ml beaker equipped with a magnetic stirrer. 1.8 grams of sodium hydroxide in 30 ml of water were added at 0° C. and the mixture stirred for 15 minutes. The diethyl ether layer was separated, washed with water, dried over magnesium sulfate, filtered, and concentrated in vacuo. The 1.6 grams of the 4-chloropyridine produced were placed into a 3-necked flask and dissolved in 45 ml of ethylene glycol dimethyl ether (DME). After cooling to −70° C., 10 ml of 1.5 molar (M) solution of lithium diisopropyl amide (LDA) in cyclohexane were added over a period of 30 minutes while maintaining the temperature below −60° C. Upon completion of the addition, the reaction mixture was stirred for an additional hour at −70° C. To this cooled mixture were then added 2.6 grams of 4-bromopyridine-3-carboxaldehyde that was dissolved in 10 ml of DME. The reaction mixture was stirred in a dry-ice bath for 2 hours and then left at room temperature overnight. 35 ml of saturated ammonium chloride solution were added to the reaction mixture, and the mixture was stirred for 15 minutes at room temperature. The mixture was then extracted twice with ethyl ether. The combined ether extracts were then washed with water, dried over magnesium sulfate, filtered, and concentrated in vacuo to afford 2.9 g of the crude product as a viscous oil. This oil was then chromatographed on a silica gel column using ethyl acetate as the eluant to afford 0.5 g of 1-(4-bromopyrid-3-yl)-1-(4-chloropyrid-3-yl)methanol as a waxy solid.

Example 2

Preparation of
1-(4-bromopyrid-3-yl)-1-(4-chloropyrid-3-yl)-
1-trimethylacetoxymethane (Compound No. 6)

0.4 grams of 1-(4-bromopyrid-3-yl)-1-(4-chloropyrid-3-yl)methanol were dissolved in 50 ml of tetrahydrofuran (THF) and cooled to 0° C. One gram of trimethylacetyl chloride was added followed by the portionwise addition of 0.5 grams of sodium hydride (60%) over a period of 15 minutes. The reaction mixture was then allowed to warm to room temperature and then stirred overnight. 50 ml of a saturated ammonium chloride solution were added and then this mixture was extracted twice with ethyl ether. The combined ether extracts were washed with a 5% aqueous solution of potassium carbonate, dried over magnesium sulfate, filtered, and concentrated in vacuo to afford 0.5 g of 1-(4-bromopyrid-3-yl)-1-(4-chloropyrid-3-yl)-1-trimethylacetoxymethane as a waxy solid.

Example 3

Preparation of
1,1-bis-(2-chloro-4-trifluoromethylpyrid-3-yl)methanol
(Compound No. 4)

To a magnetically stirred solution of 7.2 g of diisopropylamine in 100 ml of dry THF at −70° C. under a nitrogen atmosphere were added 24 ml of a 2.5M solution of n-butyl lithium in hexanes dropwise. After stirring for 15 minutes, a solution of 10 g of 2-chloro-4-trifluoromethylpyridine in 20 ml of tetrahydrofuran (THF) was added dropwise. The light brown solution was stirred at −73° C. for 45 minutes before 2 ml of dimethylformamide (DMF) were added dropwise. After another 45 minutes, another 1.5 ml of DMF were added. The solution was stirred at −73° C. for 3 minutes more before 50 ml of a saturated ammonium chloride were added to quench the reaction. The reaction mixture was extracted with 100 ml of ethyl ether. The ether layer was separated, washed with water, washed with saturated sodium chloride solution, dried over magnesium sulfate, filtered, and concentrated in vacuo to afford 9.7 g of 3-carboxaldehyde-2-chloro-4-trifluoromethylpyridine as an amber colored oil.

To a solution of 2.2 g of diisopropylamine in 30 ml of THF at −73° C. under nitrogen atmosphere were added dropwise 7.3 ml of a 2.5M solution of n-butyl lithium in hexanes. After 15 minutes, a solution of 3 g of 2-chloro-4-trifluoromethylpyridine in 5 ml of THF was added dropwise. The resulting light brown solution was stirred at −73° C. for 1 hour before a solution of 3.5 g of 3-carboxaldehyde-2-chloro-4-trifluoromethylpyridine in 5 ml of THF was added dropwise. After stirring for 30 minutes, the reaction mixture was quenched with 10 ml of a saturated ammonium chloride solution. The reaction mixture was extracted with 50 ml of ethyl ether. The ether layer was separated, washed with water, washed with saturated sodium chloride solution, dried over magnesium sulfate, filtered, and concentrated in vacuo to afford 6.6 g of the crude product as a viscous brown oil. 2.4 g of this crude material were purified via chromatography on a silica gel column using ethyl acetate-hexane (1:9) as the eluant to afford 1.6 grams of 1,1-bis-(2-chloro-4-trifluoro-methylpyrid-3-yl)methanol as a yellow solid.

Example 4

Preparation of
1,1-bis-(4-trifluoromethylpyrid-3-yl)methanol
(Compound No. 9)

To a solution of 1.4 g of 1,1-bis-(2-chloro-4-trifluoromethylpyrid-3-yl)methanol in 12 ml of methanol were added 0.8 g of magnesium oxide and 0.3 g of 5% palladium on carbon. This mixture was then shaken on a Parr hydrogenation apparatus overnight under 50 psi of hydrogen. The palladium catalyst and magnesium oxide were removed via filtration through dicalite, and the methanol filtrate was concentrated in vacuo to afford 1.6 of a yellow solid. This solid was dissolved in 25 ml of methylene chloride. The methylene chloride solution was washed with water, dried over magnesium sulfate, filtered, and concentrated in vacuo to afford 0.93 g of 1,1-bis-(4-trifluoromethylpyrid-3-yl)methanol as a yellow solid.

Example 5

Preparation of 1,1-bis-(4-trifluoromethylpyrid-3-yl)-1-trimethylacetoxymethane (Compound No. 8)

To a mixture of 0.029 g of sodium hydride in 20 ml of a 1:1 solution of benzene and dimethylformamide were added 0.25 grams of 1,1-bis-(4-trifluoromethylpyrid-3-yl)methanol. After the gas evolution had subsided, 0.14 grams of pivaloyl chloride were added. After stirring for an hour at 50° C., the reaction mixture was partitioned between 25 ml of water and 50 ml of ethyl ether. The ethyl ether layer was washed with water, washed with a saturated sodium chloride solution, dried over magnesium sulfate, filtered, and concentrated in vacuo to afford 0.24 g of the crude product as a light brown semisolid. This crude material was then purified via chromatography on a silica gel column using ethyl acetate-hexane (1:3) as the eluant to afford 0.2 g of 1,1-bis-(4-trifluoromethylpyrid-3-yl)-1-trimethylacetoxymethane as a light brown solid.

Example 6

Preparation of 1,1-bis-(4-trifluoromethylpyrid-3-yl)-1-N,N-dimethylcarbamyloxymethane (Compound No. 7)

To a suspension of 0.029 g of sodium hydride in 2 ml of THF were added 0.25 g of 1,1-bis-(4-trifluoromethylpyrid-3-yl)methanol. After the gas evolution had subsided, 0.13 g of dimethylcarbamyl chloride were added. After stirring for 20 minutes, the reaction mixture was partitioned between 25 ml of ethyl ether and 1 ml of water. The ether layer was separated, washed with a saturated sodium chloride solution, dried over magnesium sulfate, filtered, and concentrated in vacuo to afford 0.26 g of 1,1-bis-(4-trifluoromethylpyrid-3-yl)-1-N,N-dimethylcarbamyloxymethane as a light brown solid.

Example 7

Preparation of 1-(2-chloro-4-trifluoromethylpyrid-3-yl)-1-(6-chloro-4-trifluoromethylpyrimidin-5-yl)methanol (Compound No. 16)

To a solution of 1.03 g of diisopropylamine in 30 ml of THF at −73° C. under nitrogen atmosphere was added dropwise 3.6 ml of a 2.5M solution of n-butyl lithium in hexanes. After 30 min, a solution of 1.24 g of 6-chloro-4-trifluoromethylpyrimidine in 6 ml of THF was added dropwise. This solution was stirred at −70° C. for 20 min followed by dropwise addition of 1.42 g of 3-carboxaldehyde-2-chloro-4-trifluoromethylpyridine in 5 ml of THF. After stirring at −74° C. for 3.25 hours the mixture was quenched with saturated ammonium chloride and extracted twice with 50 ml of ether. The combined organic layers were dried over magnesium sulfate, filtered, and concentrated in vacuo to afford 2.58 g of a brown oil. The crude product was purified via chromatography on silica gel using ethyl acetate-hexane (1:9) as the eluant to yield 0.391 g of 1-(2-chloro-4-trifluoromethylpyrid-3-yl)-1-(6-chloro-4-trifluoromethylpyrimidin-3-yl)methanol as a viscous oil.

Example 8

Preparation of 1-(4-chloropyrid-3-yl)-1-(thien-2-yl)methanol (Compound No. 19)

15 g of 4-chloro pyridine hydrochloride were placed into 90 ml of diethyl ether in a 500 ml beaker equipped with a magnetic stirrer. 4.0 g of sodium hydroxide in 90 ml of water were added at 0° C. and the mixture stirred for 15 minutes. The diethyl ether layer was separated, washed with water, dried over magnesium sulfate, filtered, and concentrated in vacuo. The 10.3 g of the 4-chloropyridine produced were placed into a 3-necked flask and dissolved in 100 ml of ethylene glycol dimethyl ether (DME). After cooling to −70° C., 62 ml of 1.5M solution of lithium diisopropyl amide (LDA) in cyclohexane were added over a period of 30 minutes while maintaining the temperature below −60° C. Upon completion of the addition, the reaction mixture was stirred an additional hour at −70° C. To this cooled mixture were then added 10.7 g of 2-thiophenecarboxaldehyde. The reaction mixture was stirred in a dry-ice bath for 2 hours and then left at room temperature overnight. 100 ml of saturated ammonium chloride solution were added to the reaction mixture, and the mixture was stirred for 15 minutes at room temperature. The mixture was then extracted twice with ethyl ether. The combined ether extracts were then washed with water, dried over magnesium sulfate, filtered, and concentrated in vacuo to afford the crude product as a semi-solid. Trituration with hexane then afforded crystals which were isolated through filtration. 14.5 g of 1-(4-chloropyrid-3-yl)-1-(thien-2-yl)methanol were obtained.

Example 9

Preparation of 1-(4-chloropyrid-3-yl)-1-(thien-2-yl)-trimethylacetoxymethane (Compound No. 20)

2.0 g of 1-(4-chloropyrid-3-yl)-1-(thien-2-yl)methanol were dissolved in 100 ml of THF and the solution was cooled to 0° C. 3.2 g of trimethylacetyl chloride were added followed by the portionwise addition of 1.0 g of sodium hydride (60%) over a period of 15 minutes. The reaction mixture was allowed to warm to room temperature and then stirred overnight. 100 ml of a saturated ammonium chloride solution were added, and then this mixture was extracted twice with ethyl ether. The combined ether extracts were washed with a 5% aqueous solution of potassium carbonate, dried over magnesium sulfate, filtered, and then concentrated in vacuo to obtain 2.7 g of crude product. This material was then purified via chromatography on a silica gel column using ethyl acetatehexane (1:1) as the eluant to afford 1.9 g of 1-(4-chloropyrid-3-yl)-1-(thien-2-yl)-1-trimethylacetoxymethane as an oil.

Example 10

Preparation of 1-(4-chloropyrid-3-yl)-1-(thien-2-yl)-1-N,N-dimethylcarbamyloxymethane (Compound No. 21)

To a suspension of 0.5 g of sodium hydride (60%) in 100 ml of THF were added 2.0 g of 1-(4-chloropyrid-3-yl)-1-(thien-2-yl)methanol. After the gas evolution had subsided, 1.1 g of dimethylcarbamyl chloride were added. After stirring for 20 minutes, the reaction mixture was partitioned between ethyl ether and water. The ether layer was separated, washed with a saturated sodium chloride solution, dried over magnesium sulfate, filtered, and concentrated in vacuo to afford the crude product. This material was then purified via chromatography on a silica gel column using methylene chloride-ethyl acetate (5:1) as the eluant to afford 1.8 g of 1-(4-chloropyrid-3-yl)-1-(thien-2-yl)-1-N,N-dimethylcarbamyloxymethane as a solid.

Example 11

Employing processes similar to those described above, additional compounds, as listed in Tables I, II and III, were prepared.

TABLE I

| Compound No. | $R^1$ | $R^2$ | $R^3$ | $R^4$ | R | m | Y |
|---|---|---|---|---|---|---|---|
| 1  | Cl   | H | H | H  | C(O)NHCH$_3$       | 1 | 4-Cl |
| 2  | Cl   | H | H | H  | C(O)NHCH$_3$       | 0 |  |
| 3  | Cl   | H | H | H  | C(O)N(CH$_3$)$_2$  | 0 |  |
| 4  | CF$_3$ | H | H | Cl | H                | 2 | 2-Cl,4-CF$_3$ |
| 5  | Cl   | H | H | H  | H                  | 1 | 4-Br |
| 6  | Cl   | H | H | H  | C(O)C(CH$_3$)$_3$  | 1 | 4-Br |
| 7  | CF$_3$ | H | H | H  | C(O)N(CH$_3$)$_2$ | 1 | 4-CF$_3$ |
| 8  | CF$_3$ | H | H | H  | C(O)C(CH$_3$)$_3$ | 1 | 4-CF$_3$ |
| 9  | CF$_3$ | H | H | H  | H                 | 1 | 4-CF$_3$ |
| 10 | CF$_3$ | H | H | H  | C(O)NHCH$_2$CH$_3$ | 1 | 4-CF$_3$ |
| 11 | CF$_3$ | H | H | H  | C(O)NHCH$_3$      | 1 | 4-CF$_3$ |

TABLE II

| Compound No. | $R^1$ | $R^2$ | $R^3$ | $R^4$ | R | p | Y |
|---|---|---|---|---|---|---|---|
| 12 | CF$_3$ | H | H | Cl | H | 2 | 4-OCH$_3$,6-Cl |
| 13 | CF$_3$ | H | H | H  | H | 1 | 4-OCH$_3$ |
| 14 | CF$_3$ | H | H | H  | C(O)NHCH$_2$CH$_3$ | 1 | 4-OCH$_3$ |
| 15 | CF$_3$ | H | H | H  | C(O)N(CH$_3$)$_2$  | 1 | 4-OCH$_3$ |
| 16 | CF$_3$ | H | H | Cl | H | 1 | 4-CF$_3$,6-Cl |

TABLE III

| Compound No. | $R^1$ | $R^2$ | $R^3$ | $R^4$ | R | Z | m | Y |
|---|---|---|---|---|---|---|---|---|
| 17 | Cl | H | H | H | C(O)N(CH$_3$)$_2$ | O | 0 |  |
| 18 | Cl | H | H | H | C(O)NHCH$_3$      | O | 0 |  |
| 19 | Cl | H | H | H | H                 | S | 0 |  |
| 20 | Cl | H | H | H | C(O)C(CH$_3$)$_3$ | S | 0 |  |
| 21 | Cl | H | H | H | C(O)N(CH$_3$)$_2$ | S | 0 |  |
| 22 | Cl | H | H | H | H                 | N | 1 | 1-CH$_3$ |

HERBICIDAL SCREENING TESTS

Compounds listed in the foregoing tables were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

PRE-EMERGENCE HERBICIDAL SCREENING TEST

On the day preceding treatment, seeds of several different weed species were planted in sandy loam soil at a depth of 0.5 inch (1.3 cm) in individual rows using one species per row across the width of a flat. The soil was fortified with 17-17-17 fertilizer (N—P$_2$O$_5$—K$_2$O) on a weight basis and pasteurized. The weeds planted were wild oat (*Avena fatua*) (AVEFA), barnyardgrass (*Echinochloa crusgalli*) (ECHCG), green foxtail (*Setaria viridis*) (SETVI), velvetleaf (*Abutilon theophrasti*) (ABUTH), morningglory species (Ipomoea spp.) (IPOSS), wild mustard (*Sinapsis arvensis*) (SINAR) and yellow nutsedge (*Cyperus esculentus*) (CYPES). Plant densities ranged from 3 to 25 plants per row, depending upon the size of the plants.

Solutions of the test compounds were made by weighing out an appropriate amount of the test compound, for example 74.7 mg for an application rate of 4.0 kg/ha or 18.8 mg for an application rate of 1.0 kg/ha, into a 60 ml widemouth bottle, then dissolving the compound in 7.0 ml acetone containing 1% Tween 20® (polyoxyethylene sorbitan monolaurate emulsifier) and then adding 7 ml of deionized water to reach a 14 ml final volume. Tween 20® content was 0.5% v/v of the final spray volume. Additional solvents, not exceeding 2 ml, were used if needed to dissolve the compound.

The soil surface was sprayed inside an enclosed linear spray table. The flats were sprayed with the spray solution calibrated to deliver 748 L/ha. The application rate was between 0.9 and 4.0 kg/ha.

The flats were placed into a greenhouse at 21°–29° C. and watered daily by sprinkling. The degree of weed control was visually assessed and recorded 17–21 days after treatment, as percentage control compared to the growth of the same species of the same age in an untreated check flat.

The results of such pre-emergent testing are summarized in Table IV below.

POST-EMERGENCE HERBICIDAL EVALUATION

The soil was prepared and seeded with the same species and methodology described for the pre-emergence test. The flats were placed in the greenhouse at 21°–29° C. and watered by sprinkling. The seeds of the weed species were planted 10–12 days before treatment. In general, grasses were sprayed at a 3 to 4 leaf stage and broadleaves at a 1 to 2 leaf stage. Watering of the treated flats was confined to the soil surface and not to the foliage of the germinated plants. The degree of weed control was visually assessed and recorded 17–21 days after treatment, as percentage control compared to the growth of the same species in an untreated check flat of the same age.

The results of such post-emergent testing are summarized in Table V below.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill.

TABLE IV

Pre-Emergent - Testing

| COMPOUND NO. | KG/HA | AVEFA | ECHCG | SETVI | ABUTH | IPOSS | SINAR | CYPES |
|---|---|---|---|---|---|---|---|---|
| 1 | 4.0 | 80 | 100 | 100 | 10 | 100 | 10 | 50 |
| 2 | 4.0 | 0 | 0 | 10 | 0 | 0 | 0 | 0 |
| 3 | 4.0 | 0 | 5 | 15 | 0 | 0 | 0 | 0 |
| 4 | 4.0 | 5 | 25 | 60 | 10 | 10 | 10 | 0 |
| 6 | 4.0 | 10 | 100 | 100 | 5 | 100 | 20 | 70 |
| 7 | 1.0 | 98 | 100 | 100 | 98 | 95 | 85 | 100 |
| 8 | 1.0 | 98 | 100 | 100 | 100 | 98 | 85 | 75 |
| 9 | 1.0 | 30 | 100 | 80 | 0 | 5 | 0 | 70 |
| 10 | 1.0 | 98 | 100 | 100 | 95 | 95 | 80 | 100 |
| 12 | 1.0 | 0 | 0 | 10 | 10 | 0 | 0 | 0 |
| 13 | 0.9 | 0 | 0 | 0 | 0 | 10 | 0 | 0 |
| 14 | 1.0 | 98 | 100 | 100 | 85 | 98 | 75 | 80 |
| 17 | 4.0 | 0 | 0 | 10 | 0 | 0 | 0 | 0 |
| 18 | 4.0 | 0 | 0 | 15 | 0 | 0 | 0 | 0 |
| 19 | 4.0 | 0 | 0 | 5 | 10 | 0 | 0 | 0 |
| 20 | 4.0 | 0 | 15 | 50 | 0 | 0 | 10 | 0 |
| 21 | 4.0 | 0 | 10 | 40 | 0 | 0 | 0 | 0 |

TABLE V

Post-Emergent - Testing

| COMPOUND NO. | KG/HA | AVEFA | ECHCG | SETVI | ABUTH | IPOSS | SINAR | CYPES |
|---|---|---|---|---|---|---|---|---|
| 1 | 4.0 | 15 | 95 | 95 | 40 | 85 | 15 | 60 |
| 2 | 4.0 | 0 | 0 | 5 | 0 | 20 | 10 | 0 |
| 3 | 4.0 | 0 | 0 | 10 | 10 | 10 | 5 | 0 |
| 4 | 4.0 | 0 | 0 | 0 | 0 | 5 | 5 | 0 |
| 6 | 4.0 | 10 | 60 | 50 | 90 | 90 | 25 | 10 |
| 7 | 1.0 | 50 | 90 | 80 | 90 | 90 | 25 | 70 |
| 8 | 1.0 | 10 | 50 | 75 | 80 | 90 | 20 | 5 |
| 9 | 1.0 | 0 | 10 | 0 | 5 | 25 | 0 | 0 |
| 10 | 1.0 | 50 | 85 | 90 | 95 | 95 | 50 | 50 |
| 12 | 1.0 | 0 | 0 | 0 | 5 | 0 | 0 | 0 |
| 13 | 0.9 | 0 | 0 | 0 | 0 | 10 | 5 | 0 |
| 14 | 1.0 | 0 | 5 | 15 | 70 | 60 | 5 | 10 |
| 17 | 4.0 | 0 | 0 | 5 | 5 | 5 | 5 | 0 |
| 18 | 4.0 | 0 | 0 | 0 | 0 | 0 | 0 | 0 |
| 19 | 4.0 | 0 | 0 | 0 | 10 | 15 | 15 | 0 |
| 20 | 4.0 | 0 | 10 | 10 | 5 | 30 | 5 | 0 |
| 21 | 4.0 | 5 | 5 | 10 | 20 | 20 | 60 | 0 |

The results above illustrate the preemergent and postemergent efficacy of the present compounds against a variety of grass, broadleaf and perennial weed species.

Although the invention has been described with reference to preferred embodiments and examples thereof, it is not intended that the present invention be limited to only those described embodiments. The description of the preferred embodiments contained herein is intended in no way to limit the scope of the invention. As will be apparent to a person skilled in the art, modifications and adaptations of the above-described invention will become readily apparent without departure from the spirit and scope of the invention, the scope of which is defined and circumscribed by the appended claims.

What is claimed is:

1. A compound of the formula

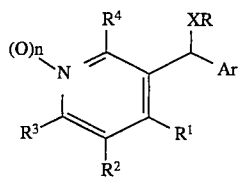

wherein:

Ar is a substituted or unsubstituted pyridyl gorup;

$R^1$, $R^2$, $R^3$ and $R^4$ are each independently hydrogen, halogen, $C_1$–$C_6$ alkyl, $C_2$–$C_6$ alkenyl, $C_2$–$C_6$ alkynyl, nitro, cyano, hydroxy, thiocyano,—$N(R^{11})$ $(R^{12})$, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy($C_1$–$C_6$)alkyl, —C(X)—$R^{10}$ or —S(O)$_k$—$R^{10}$;

X is oxygen or sulfur;

R is —C(Q)—$R^6$, —C(O)—C(O)—$R^6$, —S(O)$_2$—$R^6$, —P(Q) $(R^{11})$ $(R^{12})$ or —Si$(R^{13})$ $(R^{14})$ $(R^{15})$; wherein:

Q is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$) ($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$) ($R^{10}$) wherein $R^9$ and R 10 are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_{1-C6}$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl;

k is 0, 1 or 2; and n is 0 or 1;

or an agriculturally acceptable salt thereof.

2. A compound of the formula

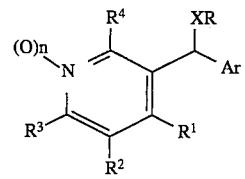

wherein:

Ar is a substituted or unsubstituted pyridyl group $R^1$, $R^2$, $R^3$ and $R^4$ are each independently hydrogen, halogen, $C_1$–$C_6$ alkyl, $C_2$–$C_6$ alkenyl, $C_2$–$C_6$ alkynyl, nitro, cyano, hydroxy, thiocyano, —$N(R^{11})$ $(R^{12})$, $C_1$–$C_6$ haloalkyl, $C_1$–$C_6$ alkoxy, $C_1$–$C_6$ haloalkoxy, ($C_1$–$C_6$)alkoxy-($C_1$–$C_6$)alkyl, halo($C_1$–$C_6$)alkoxy($C_1$–$C_6$)alkyl, —C(X)—$R^{10}$ or —S(O)$_k$—$R^{10}$ with the proviso that one of $R^1$, $R^2$, $R^3$ and $R^4$ is other than hydrogen; X is oxygen or sulfur;

R is of the formula —C(Q)—$R^6$, —C(O)—C(O)—$R^6$, —S(O)$_2$—$R^6$, —P(Q)$(R^{11})$ $(R^{12})$ or —Si$(R^{13})$ $(R^{14})$ $(R^{15})$, wherein:

Q is oxygen or sulfur;

$R^6$ is hydrocarbyl, substituted hydrocarbyl, hydrocarbyloxy, substituted hydrocarbyloxy, hydrocarbyl-S—, substituted hydrocarbyl-S— or is of the formula —N($R^7$) ($R^8$);

wherein $R^7$ and $R^8$ are each independently hydrogen, hydrocarbyl, substituted hydrocarbyl, hydrocarbyloxy, substituted hydrocarbyloxy, pyridyl, furyl, thienyl, ($C_1$–$C_6$)alkoxycarbonyl($C_1$–$C_6$)alkyl, hydroxycarbonyl($C_1$–$C_6$)alkyl, or N($R^9$) ($R^{10}$) wherein $R^9$ and R 10 are each independently hydrogen, $C_1$–$C_6$ alkyl or phenyl;

or $R^7$ and $R^8$ together with the nitrogen to which they are bound form an aziridine, piperazine, morpholine, thiomorpholine, thiomorpholine 1-oxide, thiomorpholine 1,1-dioxide, hexamethyleneimine, piperidine or pyrrolidine ring, any of which may be optionally substituted with $C_1$–$C_6$ alkyl;

$R^{11}$ and $R^{12}$ are each independently $C_1$–$C_6$ alkyl, $C_1$–$C_6$ alkylthio or $C_{1-C6}$ alkoxy;

$R^{13}$, $R^{14}$ and $R^{15}$ are each independently $C_1$–$C_6$ alkyl, $C_1$–$C_6$ alkoxy, $C_1$–$C_6$ haloalkyl, aryl or arylalkyl;

k is 0, 1 or 2; and n is 0 or 1;

or an agriculturally acceptable salt thereof.

3. A compound as defined in claim 1, or an agriculturally acceptable salt thereof, wherein Ar is a substituted or unsubstituted pyridyl group; $R^1$, $R^2$, $R^3$ and $R^4$ are each independently hydrogen, halogen, $C_1$–$C_6$ alkyl, $C_1$–$C_6$ haloalkyl, $C_1$–$C_6$ alkoxy, $C_1$–$C_6$ haloalkoxy, nitro or —S(O)$_k$—($C_1$–$C_3$) alkyl wherein k is 0, 1 or 2; and R is of the formula

wherein $R^6$ is $C_1$–$C_{12}$ alkyl, $C_1$–$C_6$ haloalkyl, phenyl or is N($R^7$) ($R^8$), wherein $R^7$ and $R^8$ are each independently $C_1$–$C_{12}$ alkyl, hydrogen, $C_2$–$C_{12}$ alkynyl, $C_1$–$C_{12}$ haloalkyl, $C_1$–$C_6$ alkoxy, ($C_1$–$C_6$)alkoxy($C_1$–$C_6$)alkyl or $R^7$ and $R^8$ together with the nitrogen to which they are bound form a morpholine, piperidine or pyrrolidine ring.

4. A compound as defined in claim 1, or an agriculturally acceptable salt thereof, wherein Ar is a substituted or unsubstituted pyridyl group;

$R^1$ is trifluoromethyl, fluoro, chloro, bromo, iodo, methoxy, methyl or ethyl;

$R^2$, $R^3$ and $R^4$ are each independently hydrogen, chloro or bromo;

X is oxygen; and

R is of the formula

wherein $R^6$ is $C_1$–$C_6$ alkyl or is of the formula $N(R^7)(R^8)$, wherein $R^7$ is $R^8$ are independently hydrogen, $C_1$–$C_6$ haloalkyl, $C_1$–$C_6$ alkyl or $C_2$–$C_6$ alkenyl.

5. A compound as defined in claim 1, or an agriculturally acceptable salt thereof, having the formula wherein

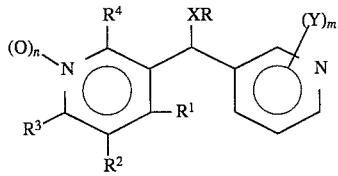

X, $R^1$, $R^2$, $R^3$, and $R^4$ and n have the same meanings as in claim 1;

m is 0, 1, 2, 3 or 4; and when m is not 0, each Y is independently hydrogen, halogen, $C_1$–$C_6$ alkyl, $C_1$–$C_6$ haloalkyl, $C_1$–$C_6$ alkoxy, $C_2$–$C_6$ alkenyl, $C_2$–$C_6$ alkynyl, $C_1$–$C_6$ alkylcarbamylthio, mercapto, $C_1$–$C_6$ haloalkoxy, nitro cyano, hydroxy, thiocyano, ($C_1$–$C_6$)-alkoxy-($C_1$–$C_6$)alkyl, —S(O)$_k$—$R^{10}$ or —N($R^{11}$)($R^{12}$), wherein k, $R^{10}$, $R^{11}$ and $R^{12}$ have the same meanings as in claim 1.

6. A compound as defined in claim 1, wherein X is oxygen and R is hydrogen.

7. An herbicidal composition comprising an herbicidally effective amount of a compound according to claim 1, or an agriculturally acceptable salt thereof, and an agriculturally acceptable carrier therefor.

8. An herbicidal composition comprising an herbicidally effective amount of a compound according to claim 2, or an agriculturally acceptable salt thereof, and an agriculturally acceptable carrier therefor.

9. An herbicidal composition comprising an herbicidally effective amount of a compound according to claim 4, or an agriculturally acceptable salt thereof, and an agriculturally acceptable carrier therefor.

10. An herbicidal composition comprising an herbicidally effective amount of a compound according to claim 5, or an agriculturally acceptable salt thereof, and an agriculturally acceptable carrier therefor.

11. An herbicidal composition comprising an herbicidally effective amount of a compound according to claim 6, or an agriculturally acceptable salt thereof, and an agriculturally acceptable carrier therefor.

12. A method for controlling undesirable vegetation comprising applying to an area where control is desired an herbicidally effective amount of a compound according to claim 1, or an agriculturally acceptable salt thereof.

13. A method for controlling undesirable vegetation comprising applying to an area where control is desired an herbicidally effective amount of a compound according to claim 3, or an agriculturally acceptable salt thereof.

14. A method for controlling undesirable vegetation comprising applying to an area where control is desired an herbicidally effective amount of a compound according to claim 4, or an agriculturally acceptable salt thereof.

15. A method for controlling undesirable vegetation comprising applying to an area where control is desired an herbicidally effective amount of a compound according to claim 5, or an agriculturally acceptable salt thereof.

16. A method for controlling undesirable vegetation comprising applying to an area where control is desired an herbicidally effective amount of a compound according to claim 6, or an agriculturally acceptable salt thereof.

* * * * *